(12) United States Patent
Divoky et al.

(10) Patent No.: US 10,011,014 B2
(45) Date of Patent: Jul. 3, 2018

(54) DETERMINING A UNIQUE SPATIAL RELATIONSHIP OF A MEDICAL DEVICE TO A FURTHER OBJECT

(71) Applicants: Robert Divoky, Forchheim (DE); Philip Mewes, Nürnberg (DE)

(72) Inventors: Robert Divoky, Forchheim (DE); Philip Mewes, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 18 days.

(21) Appl. No.: 15/097,451

(22) Filed: Apr. 13, 2016

(65) Prior Publication Data

US 2016/0297074 A1      Oct. 13, 2016

(30) Foreign Application Priority Data

Apr. 13, 2015   (DE) .................. 10 2015 206 511

(51) Int. Cl.
| | |
|---|---|
| *B25J 9/16* | (2006.01) |
| *B25J 13/02* | (2006.01) |
| *A61B 34/30* | (2016.01) |

(52) U.S. Cl.
CPC ............ *B25J 9/1674* (2013.01); *A61B 34/30* (2016.02); *B25J 9/1689* (2013.01); *B25J 9/1692* (2013.01);
(Continued)

(58) Field of Classification Search
CPC ...... B25J 9/1674; B25J 9/1689; B25J 9/1692; B25J 9/1697; Y10S 901/02; Y10S 901/09;
(Continued)

(56) References Cited

U.S. PATENT DOCUMENTS

| | | | | |
|---|---|---|---|---|
| 3,986,007 A | * | 10/1976 | Ruoff, Jr. ................. | B25J 15/08 250/548 |
| 5,086,401 A | * | 2/1992 | Glassman ............. | A61B 34/20 606/53 |

(Continued)

FOREIGN PATENT DOCUMENTS

DE      102008025151 A1      12/2008

OTHER PUBLICATIONS

German office Action for related German Application No. 10 2015 206 511.1 dated Nov. 24, 2015, with English Translation.
(Continued)

*Primary Examiner* — Bao Long T Nguyen
(74) *Attorney, Agent, or Firm* — Lempia Summerfield Katz LLC

(57) ABSTRACT

The present embodiments relate to a method for determining a unique spatial relation of a medical device to an object. The medical device includes a registration mechanism with a first determination of the spatial relation of the medical device to the object by the registration mechanism by a first method for determining a relation of this kind, and with a second determination of the spatial relation of the medical device to the object by the registration mechanism by a second method for determining a relation of this kind. The second method is based on a physical principle of action different from that of the first method, with an evaluation of the results of the first and second determinations with respect to conformance by the registration mechanism, and, on the determination of a prespecified degree of conformance between the results, with a final determination of the spatial relation from the results of the first and second determinations by the registration mechanism to increase the safety of the medical device during operation in spatial interaction with a object.

11 Claims, 1 Drawing Sheet

(52) U.S. Cl.
CPC ........... *B25J 9/1697* (2013.01); *B25J 13/025* (2013.01); *Y10S 901/02* (2013.01); *Y10S 901/09* (2013.01)

(58) Field of Classification Search
CPC ..... G05B 2219/40572; G05B 19/401–19/4015
USPC ............ 700/254, 258, 259; 901/2, 9, 46, 47; 318/568.24; 702/85, 94, 97
See application file for complete search history.

(56) References Cited

U.S. PATENT DOCUMENTS

| | | | |
|---|---|---|---|
| 6,288,785 B1* | 9/2001 | Frantz | A61B 5/06 250/559.29 |
| 2007/0265527 A1* | 11/2007 | Wohlgemuth | A61B 6/547 600/424 |
| 2011/0077504 A1* | 3/2011 | Fischer | A61B 34/30 600/411 |
| 2013/0096573 A1* | 4/2013 | Kang | A61B 34/30 606/130 |
| 2015/0305701 A1 | 10/2015 | Wendler et al. | |
| 2016/0030117 A1* | 2/2016 | Mewes | A61B 19/2203 600/424 |

OTHER PUBLICATIONS

Gulhar, Abhinav, Mewes, Philip: "Registration of Navigation Systems" in: Prior Art Journal 01—pp. 240-242—ISBN: 978-3-945188-04-0, 2015.

* cited by examiner

DETERMINING A UNIQUE SPATIAL RELATIONSHIP OF A MEDICAL DEVICE TO A FURTHER OBJECT

CROSS-REFERENCE TO RELATED APPLICATIONS

The present patent document claims the benefit of DE 102015206511.1, filed on Apr. 13, 2015, that is hereby incorporated by reference in its entirety

BACKGROUND

The present embodiments relate to a method for determining a unique spatial relation of a medical device to an object. The medical device includes a registration mechanism. The embodiments also relate to a medical device with a registration mechanism by which a spatial relation of the medical device to an object may be determined by a first method for determining a relation of this kind.

In medical scenarios, there may be interaction between at least one medical device and an object (e.g., a patient or another medical device). At the same time, in many cases, it is decisive that a medical device has a prespecified unique spatial relation to the object so that movements of the medical device or a movable component of the medical device take place in a precise relative position (e.g., a unique spatial relation to the object). The determination of the spatial relation of the medical device to the object is also referred to as registration. In many scenarios, this registration is relevant for the safety of patients and staff (e.g., to avoid collisions between medical devices or medical devices and patients).

For example, a registration that takes place using a contact-free method in an image-based manner (e.g., with the "Mako" robot using fluorescence-based markers) may be afflicted with errors. An error of this kind is particularly critical if the error may have a fatal outcome. For example, errors may occur in a robotic minimally invasive surgical intervention by a medical device in which a medical robotic device performs autonomous movements in the patient or in the vicinity of the patient and these movements are controlled by image data to which the medical device was possibly incorrectly registered (e.g., incorrectly placed in a unique spatial relationship).

If fatal events of this kind are at all feasible, it must not be possible for one single error to be sufficient to allow a fatal event of this kind actually to take place. Preventing all critical errors from occurring is known as the so-called first-fault safety. One possibility of achieving this first-fault safety is to anchor the medical device to a firmly defined position relative to the object. For example, anchoring the medical device is achieved by the "Perfint" system where the medical device is firmly anchored in the ground. However, anchoring the medical device restricts the flexibility of the positioning of the medical devices to an extreme degree.

SUMMARY AND DESCRIPTION

The scope of the present is defined solely by the appended claims and is not affected to any degree by the statements within this summary.

The present embodiments may obviate one or more of the drawbacks or limitations in the related art. For example, the present embodiments increase the safety of a medical device during operation in spatial interaction with an object a patient or a further medical device).

The present embodiments relate to a method for determining a unique spatial relation of a medical device (e.g., a robotic device) or a movable component of such a device to an object. Determining the spatial relation may entail an automatic determination or a semi-automatic determination. The movable component may be an end effector of a kinematic chain of the robotic medical device. At the same time, the medical device includes a registration mechanism.

The method includes a series of acts. A first determination of the spatial relation of the medical device to the object is performed by the registration mechanism by a first method for determining a spatial relation (e.g., a first registration). A second determination of the spatial relation of the medical device to the object is performed by the registration mechanism by a second method for determining a spatial relation (e.g., a second registration). The second method is based on a physical principle of action different from that of the first method. The determination of the spatial relation of the medical device to the object by the registration mechanism may be performed redundantly, and/or there is a redundant registration of the medical device to the object.

Evaluation of the results of the first and second determinations with respect to conformance of the results is performed by the registration mechanism. Based on the determination of a prespecified degree of conformance between the results, a final determination of the spatial relation from the results of the first and second determinations is performed by the registration mechanism. A high degree of conformance may be achieved if the respective results of the first and second determinations represent a very similar or identical spatial relation, or such a very similar or identical spatial relation may he derived from the respective results. For example, the degree of conformance may he included in the spatial distance resulting from the spatial relation. With respect to the requirements to avoid collision between two systems, it is advantageous to specify a maximum spatial distance of 15 cm (e.g., a maximum spatial distance of 2 cm as a limit value for the conformance). At least one of the two registration methods may be significantly more accurate if it is to be used for diagnostic purposes.

Safety is increased because the probability of two results that are independent of one another and based on different principles of action of the respective registration (e.g., of the first and second determinations) being wrong simultaneously is extremely low. If a determination produces a faulty result, it is highly probable that the conformance of the results is low. In addition, the use of two registration methods, or a double determination of the spatial relation of the medical device to the object, may increase the overall accuracy.

In one embodiment, based on the determination of a degree of conformance that is below the prespecified degree of conformance, the low degree of conformance is signaled. In particular, the signaling may be performed by marking a result of the evaluation as faulty. The marking may be a marking of a data set assigned to the result. The evaluation may include a comparison of the results of the first and second determinations and a check whether a comparative result exceeds a prespecified limit value. Exceeding the prespecified limit value may then be signaled.

In the event of different or clearly different results of the first and second determinations, the occurrence of which is indicative of a faulty determination or a faulty registration, the result of the evaluation is marked and use of results with potentially fatal consequences may be forestalled. The signaling may also draw the attention of an operator or a monitoring algorithm of the registration mechanism to the faulty registration. The registration mechanism and/or operator may then react appropriately and prevent damage to people or medical devices.

At the same time, the signaling may include the display of an error message and/or a prompt for the method to be performed again. This display may be directed at an operator. This has the advantage that even an untrained operator knows immediately how the error is to be rectified or the quickest way for the error to be rectified, and following the achievement of an error-free registration, the medical process may be continued as quickly as possible.

In an embodiment, a prespecified functionality of the medical device may exclusively be, or only be, activated when the prespecified degree of conformance has been identified. The prespecified functionality may also include a prespecified operational act to be performed by the medical device in a sequence of operations (e.g., at a prespecified time). A comparable or identical operational act may be performed at a time different from the prespecified time.

In the case of a poor degree of conformance (e.g., one that falls below the prespecified degree), the erroneous use of the prespecified functionality is automatically prevented and a risk to a patient or damage to a medical device due to human error (e.g., an operator who overlooks the signaling of a faulty result of the evaluation) is prevented, increasing the safety.

For example, the medical device may be a robotic device and the prespecified functionality includes a mobility and/or an autonomous movement of the robotic device, or a movable component of the robotic device (e.g., an end effector of a kinematic chain of the robotic device). As described in the previous paragraph, the blocking of the prespecified functionality is particularly advantageous because a mobile medical robotic device (e.g., a medical robotic device) that is able to move autonomously on or in a patient may have particularly serious consequences in the event of a faulty registration.

In an embodiment, the first method is a contact-free method. The contact-free method may he an image-based method (e.g., based on visible light, X-rays, and/or infrared light). Generally established medical devices requiring registration may carry out the first method for the registration, and the method may be used to increase safety in these medical devices. It has been found that (e.g., with X-ray imaging systems) registration with a high degree of accuracy may be achieved with the spatial error of an order of magnitude of less than 1 mm. Registration accuracy of an order of magnitude of less than 1 mm inter alia satisfies the requirements to be imposed for use for diagnostic purposes.

In an embodiment, the medical device is a robotic device and the second method is a haptic method. With the haptic method, the robotic medical device (e.g., an end effector of a kinematic chain of the medical device) approaches at least one predetermined position or pose on the object in order to determine the spatial relation of the medical device to the object. A predetermined pose may be understood to be a predetermined position with a predetermined orientation. Safety is increased precisely for dangerous medical devices (e.g., robotic medical devices). Because the second method is a haptic method and no special measuring equipment is required (e.g., similar to with an image-based method for the registration), the haptic method may also be used for the registration of conventional robotic medical devices. In the case of doubt, registration of conventional robotic medical devices may be performed with slight adaptations (e.g., such as with firmware or software updates). The second method may be used particularly flexibly. The predetermined position or pose may also be specified depending on the respective object. For example, the method for the registration may not only be used in medical robotic devices that are already in use in prespecified medical scenarios, but may also be configured to the object. The safety is increased for a plurality of different medical devices and different objects. It has been found that haptic methods automatically enable registration with an accuracy with which the spatial error has an order of magnitude of a few centimeters.

The robotic medical device may approach the predetermined position or the predetermined pose with guidance from an operator. Guidance from an operator has the advantage that the robotic device does not need any sensor technology for the second method for the registration, other than that already provided in commercially available robotic medical devices. Requiring no additional sensor technology enlarges the field of application of the method and may increase safety during the use of medicinal devices.

The robotic device approaches two, three or four predetermined positions depending on the number of degrees of freedom of the robotic device. In the case of two degrees of freedom (e.g., translatory), it is possible for two or three predetermined positions to be approached and, in the case of three degrees of freedom translatory), for three or four predetermined positions to be approached. Either the second method for the registration may be performed with the lowest number of predetermined positions (e.g., particularly quickly) or, with an additional position, the second method for the registration may be performed particularly accurately and a particularly accurate result is achieved. Safety may be increased in accordance with the respective requirements depending on the underlying medical conditions.

The present embodiments also relate to a medical device with a registration mechanism that determines a spatial relation of the medical device to an object by a first method for determining a spatial relation. The registration mechanism is also able to determine the spatial relation of the medical device to the object by a second method for determining a spatial relation. The second method is based on a different physical principle of action from that of the first method. Moreover, the registration mechanism is able to evaluate the results of the first and second determinations with respect to conformance and, based on the determination of a prespecified degree of conformance between the results, the registration mechanism determines the spatial relation from the results of the first and second determinations.

All the above features and combinations of features named above in the description and named below in the description of the figures and/or features and combinations of features shown alone in the figures can he used not only in the respective combination disclosed, but also in other combinations or on their own, without departing from the scope of the invention. Hence, embodiments which are not explicitly shown and explained but can be derived and produced from the illustrated embodiments by separated feature combinations should be regarded as being comprised and disclosed by the invention.

DETAILED DESCRIPTION

Figure 1:
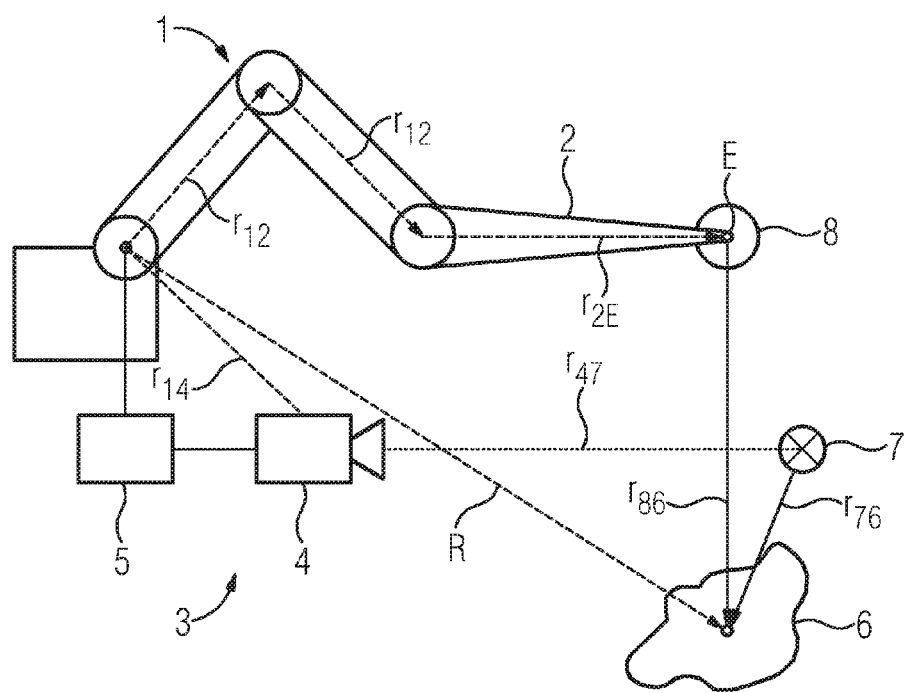
FIG. 1 depicts a schematic representation of a method for determining a unique spatial relation with reference to a medical device in a first exemplary embodiment.

FIG. 1 is a schematic representation of a method for determining a unique spatial relation with reference to a medical device in a first exemplary embodiment.

The medical device 1 is provided as a robotic medical device 1 and includes an end effector 2. A registration mechanism 3 (e.g., a camera 4 and a control mechanism 5) is also included in the medical device 1. The medical device ay be registered to an object 6. A unique spatial relation R of the medical device 1 (e.g., a base of the medical device 1) to the object 6 is determined. As depicted in FIG. 1, two reference positions 7 and 8 are used, which are in known spatial relations $r_{76}$ and $r_{86}$ to the object 6.

As depicted in FIG. 1, first a dotted line symbolizes the acquisition of the optical reference position 7 and the spatial relation $r_{47}$ of the camera 4 to the reference position 7. Because the spatial relation $r_{14}$ between the camera 4 and medical device 1 (e.g., the base of the medical device 1) is known, it is possible to determine the spatial relation R of the medical device 1 (and in derivation therefrom, also of the end effector 2 and an end point E of the end effector) to the object 6. In the example shown, the first determination act 10 (FIG. 2) of the spatial relation R of the medical device 1 to the object 6 by the registration mechanism 3 is determined (e.g., with a contactless image-based method).

In the example shown, a second determination act 11 (FIG. 2) of the spatial relation R of the medical device 1 to the object 6 is performed using a haptic method. For example, the end point E of the end effector 2 is guided by an operator ne or more reference positions (e.g., the one second reference position 8). The spatial elation R of the medical device 1 to the further object 6 may be determined again independently of the camera 4 and the first method from the known spatial relations $r_{12}$ of the robotic device 1 to the end effector 2, the known spatial relation $r_{2E}$ of the end effector 2 to the end point E, and the known spatial relation $r_{86}$ of the second reference point 8 to the object 6.

The results of the first and second determinations may be evaluated. If a prespecified degree of conformance between the results is determined, a final determination of the spatial relation R may be performed because the relation R in all probability reflects reality with sufficient accuracy. If however, the prespecified degree of conformance may not be determined, at least one of the two registrations is faulty and the use of the medical device 1 or the end effector 2 may have serious consequences, and use may be avoided by blocking a functionality of the medical device 1 or the end effector 2.

Figure 2:
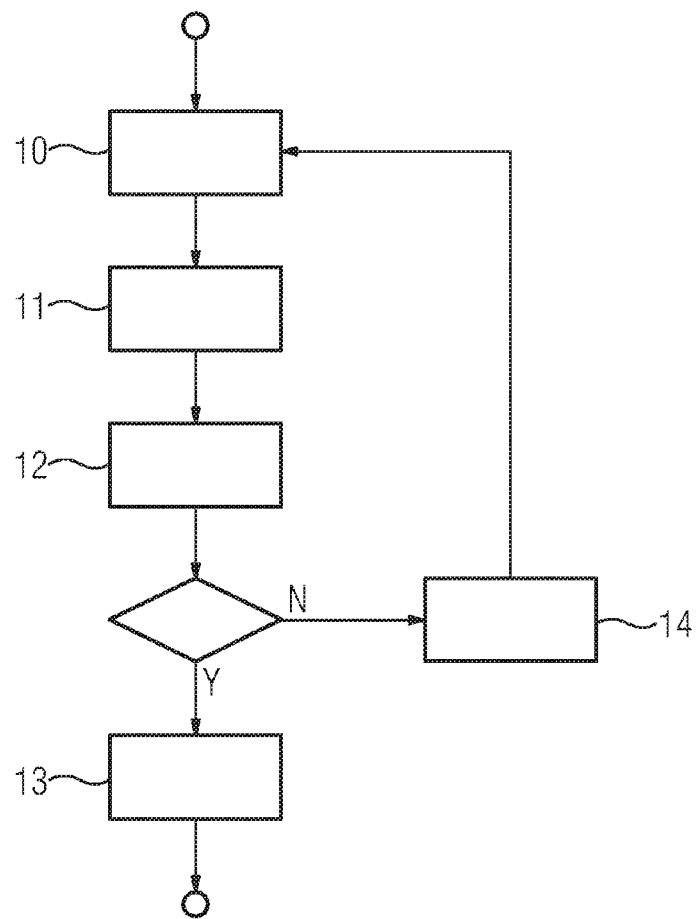
FIG. 2 depicts a schematic flow diagram of a further exemplary embodiment of a method for determining a unique spatial relation.

FIG. 2 is a schematic flow diagram of an exemplary embodiment of a method for determining a unique spatial relation.

In the example shown, the first act is a first determination 10 of the spatial relation R (FIG. 1) of the medical device 1 (FIG. 1) to the object 6 (FIG. 1) by the registration mechanism 3 (FIG. 1) by a first method for the registration or determination of a spatial relation. For example, the medical device 1 may be provided as a lightweight robot and registered via an image-based method as shown in FIG 1 to a C-Arm system as the object 6.

A second determination 11 of the spatial relation R (FIG. 1) of the medical device 1 (FIG. 1) to the object 6 (FIG. 1) by the registration mechanism 3 (FIG. 1) by a second method for determining a spatial relation or for the registration. For example, the second method may be a haptic method. For example, the lightweight robot may approach different predetermined reference positions 7 and 8 (FIG. 1) on a component of the C-Arm system.

Accordingly, both methods provide a registration. This is represented mathematically by a transformation matrix with that may include six degrees of freedom between two coordinate systems. In the method shown, evaluation 12 of the respective results of the first and second determinations 10 and 11 with respect to conformance by the registration mechanism 3 (FIG. 1) is performed. If a prespecified degree of conformance between the results is established, there is a final determination 13 of the spatial relation R (FIG. 1) from the results of the first and second determinations 10 and 11 by the registration mechanism 3. For example, the determination may be performed using vectors that represent the relation of the medical device 1 to the object 6 according to the different methods.

If the degree of conformance established between the results is not the prespecified degree of conformance (e.g., fails to achieve the prespecified degree) the low degree of conformance is signaled 14, followed by a repeated performance of the method. This provides that the spatial relation R between the medical device 1 and the object 6 is determined with particular accuracy and high reliability.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it he understood that all equivalents and/or combinations of embodiments are intended to he included in this description.

The invention claimed is:

1. A method for determining a unique spatial relation of a medical device to an object, wherein the medical device comprises a registration mechanism, the method comprising:

determining a first determination of the spatial relation of the medical device to the object by the registration mechanism by a first method for determining a spatial relation;

determining a second determination of the spatial relation of the medical device to the object by the registration mechanism by a second method for determining a spatial relation, wherein the second method is based on a physical principle of action different from that of the first method;

evaluating results of the first and second determinations with respect to a conformance by the registration mechanism, wherein the conformance represents a similarity between the results of the first and second determinations of the spatial relation;

determining, based on determining that the conformance is above a prespecified degree of conformance between the results, a final determination of the spatial relation from the results of the first and second determinations by the registration mechanism; and signaling, based on determining that the conformance is below the prespecified degree of conformance, a low degree of conformance, wherein the signaling comprises display of an error message, a prompt that the method is to be performed again, or the error message and the prompt that the method is to be performed again.

2. The method of claim 1, wherein a prespecified functionality of the medical device is configured to be activated only when the prespecified degree of conformance has been established.

3. The method of claim 2, wherein:

the medical device is a robotic device; and the prespecified functionality comprises a mobility, an autonomous movement, or both the mobility and the autonomous movement of the robotic device or a component of the robotic device.

4. The method of claim 3, wherein the first method is a contact-free method.

5. The method of claim 4, wherein the first method is an image-based method based on visible light, X-rays, infrared light, or a combination thereof.

6. The method of claim 5, wherein the second method is a haptic method with that the robotic device approaches at least one predetermined position or pose on the object to determine the spatial relation of the medical device to the object.

7. The method of claim 6, wherein the robotic device approaches the predetermined position or pose with guidance from an operator.

8. The method of claim 6, wherein the robotic device approaches two, three, or four predetermined positions depending on a number of degrees of freedom of the robotic device.

9. The method of claim 7, wherein the robotic device approaches two, three, or four predetermined positions depending on a number of degrees of freedom of the robotic device.

10. The method of claim 1, wherein the medical device is a robotic device and the second method is a haptic method with that the end effector of the robotic device approaches at least one predetermined position or pose on the object to determine the spatial relation of the medical device to the object.

11. A medical device comprising:

a registration mechanism configured to:

determine a spatial relation of the medical device to an object by a first method for determining a spatial relation;

determine the spatial relation of the medical device to the object by a second method for determining a spatial relation, wherein the second method is based on a physical principle of action different from that of the first method; and evaluate the results of the first and second determinations with respect to conformance, wherein the conformance represents how similar the spatial relation of the medical device to an object by a first method is to the spatial relation of the medical device to the object by a second method;

determine, when the conformance meets a prespecified degree of conformance between the results of the first and second determinations by the registration mechanism, the spatial relation from the results of the first and second determinations; and signal, when the conformance fails to meet the prespecified degree of conformance between the results of the first and second determinations by the registration mechanism, a low degree of conformance by marking a result of the evaluation as faulty.

* * * * *